United States Patent
Ting et al.

(10) Patent No.: US 8,657,753 B2
(45) Date of Patent: Feb. 25, 2014

(54) METHOD OF DERIVING CENTRAL AORTIC SYSTOLIC PRESSURE VALUES AND METHOD FOR ANALYSING AN ARTERIAL DATASET TO DERIVE THE SAME

(75) Inventors: Choon Meng Ting, Singapore (SG); Ngak Hwee Chua, Singapore (SG); Wee Leng Peh, Singapore (SG)

(73) Assignee: Healthstats International Pte Ltd, Singapore (SG)

( * ) Notice: Subject to any disclaimer, the term of this patent is extended or adjusted under 35 U.S.C. 154(b) by 235 days.

(21) Appl. No.: 13/132,410

(22) PCT Filed: Dec. 5, 2008

(86) PCT No.: PCT/SG2008/000468
§ 371 (c)(1),
(2), (4) Date: Jun. 2, 2011

(87) PCT Pub. No.: WO2010/064993
PCT Pub. Date: Jun. 10, 2010

(65) Prior Publication Data
US 2011/0230773 A1    Sep. 22, 2011

(51) Int. Cl.
*A61B 5/021* (2006.01)
(52) U.S. Cl.
USPC .......................................... 600/485; 600/481
(58) Field of Classification Search
USPC .................................................. 600/485, 481
See application file for complete search history.

(56) References Cited

U.S. PATENT DOCUMENTS

| | | | |
|---|---|---|---|
| 5,265,011 A | 11/1993 | O'Rourke | |
| 5,746,698 A | 5/1998 | Bos et al. | |
| 2006/0189872 A1 | 8/2006 | Arnold | |
| 2008/0306393 A1* | 12/2008 | Ting et al. | 600/485 |

OTHER PUBLICATIONS

Fetics et al. "Parametric Model Derivation of Transfer Function for Noninvasive Estimation of Aortic Pressure by Radial Tonometry," IEEE Trans. Biomed. Eng., 1999, vol. 46(6), pp. 698-706.

* cited by examiner

*Primary Examiner* — Navin Natnithithadha
*Assistant Examiner* — Meredith Weare
(74) *Attorney, Agent, or Firm* — MKG, LLC

(57) ABSTRACT

A method, system and computer readable medium for deriving central aortic systolic pressure by reversing the order of a set of predetermined number of blood pressure measurements to obtain a reversed blood pressure set; averaging the reversed blood pressure set such that the average set represents a moving average waveform; overlaying the reversed blood pressure set and the moving average waveform; identifying a point of intersection on the reversed arterial waveform and the moving average waveform, and setting the central aortic systolic pressure as a reversed blood pressure value in the reversed blood pressure set nearest to the point of intersection.

37 Claims, 4 Drawing Sheets

| x-coordinate | Step 12 | Step 14 | Step 18-22 |
|---|---|---|---|
| Time, second | Original data of arterial waveform captured | Reversed arterial waveform data listed in Step 12 | Regenerated data using 12 points forward moving average method from Step 14 |
| 0.017 | 85.0 | 85.0 | 88.3 |
| 0.033 | 86.0 | 85.7 | 88.9 |
| 0.050 | 88.9 | 86.6 | 89.6 |
| 0.067 | 96.8 | 87.9 | 90.3 |
| 0.083 | 107.9 | 88.1 | 90.9 |
| 0.100 | 119.2 | 88.2 | 91.7 |
| 0.117 | 126.1 | 88.2 | 92.6 |
| 0.133 | 128.0 | 88.5 | 93.6 |
| 0.150 | 126.6 | 88.4 | 94.6 |
| 0.167 | 124.2 | 89.6 | 95.6 |
| 0.183 | 121.1 | 90.5 | 96.5 |
| 0.200 | 118.8 | 92.5 | 97.4 |
| 0.217 | 117.5 | 93.0 | 98.1 |
| 0.233 | 116.8 | 93.9 | 99.3 |
| 0.250 | 115.6 | 94.4 | 100.7 |
| 0.267 | 111.2 | 95.8 | 102.5 |
| 0.283 | 106.5 | 97.6 | 104.2 |
| 0.300 | 101.9 | 99.0 | 105.9 |
| 0.317 | 100.5 | 100.1 | 107.5 |
| 0.333 | 100.3 | 100.5 | 109.3 |
| 0.350 | 100.5 | 100.5 | 111.2 |
| 0.367 | 100.5 | 100.3 | 113.4 |
| 0.383 | 100.1 | 100.5 | 115.7 |
| 0.400 | 99.0 | 101.9 | 117.9 |
| 0.417 | 97.6 | 106.5 | 119.3 |
| 0.433 | 95.8 | 111.2 | 119.4 |
| 0.450 | 94.4 | 115.6 (CASP$_{A1}$) | 118.2 |
| 0.467 | 93.9 | 116.8 (CASP$_A$) | 116.0 |
| 0.483 | 93.0 | 117.5 (CASP$_{A2}$) | 113.4 |
| 0.500 | 92.5 | 118.8 | 110.7 |
| 0.517 | 90.5 | 121.1 | 110.0 |
| 0.533 | 89.6 | 124.2 | 108.9 |
| 0.550 | 88.4 | 126.6 | 107.2 |
| 0.567 | 88.5 | 128.0 | 104.7 |
| 0.583 | 88.2 | 126.1 | 101.4 |
| 0.600 | 88.2 | 119.2 | 97.3 |
| 0.617 | 88.1 | 107.9 | 92.9 |
| 0.633 | 87.9 | 96.8 | 89.2 |
| 0.650 | 86.6 | 88.9 | 86.6 |
| 0.667 | 85.7 | 86.0 | 85.5 |
| 0.683 | 85.0 | 85.0 | 85.0 |

FIGURE 3a

METHOD OF DERIVING CENTRAL AORTIC SYSTOLIC PRESSURE VALUES AND METHOD FOR ANALYSING AN ARTERIAL DATASET TO DERIVE THE SAME

FIELD OF THE INVENTION

The invention relates to a method of deriving central aortic systolic pressure values and a method of analysing arterial waveform data to derive central aortic systolic pressure values.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as of the priority date of the application.

Heart disease is a serious health problem in developed countries. One indicator of potential heart disease is variances in the blood pressure from a designated range of "normal" values.

A common method of determining blood pressure values is to take both a systolic and diastolic blood pressure reading at a brachial artery using a pressure cuff. These values are commonly considered indicative of the general blood pressure in other arteries including the aortic pressure values. While this assumption has historically been beneficial in indicating potential heart disease, recent studies have shown that a "normal" brachial blood pressure value measured in this manner may mask abnormal central aortic systolic pressure values.

One solution to this problem has been adopted by Atcor Medical Pty Ltd. Atcor's solution uses a general transfer function formula to convert a radial pressure waveform to a central aortic blood pressure waveform. However, this general transfer formula assumes that all aortas are the same, the formula is based on a correlation value determined through testing on a cross-representation of patients and therefore the general assumption may introduce error in calculations of central aortic pressure from patients that fall outside the realms of the cross-representative sample. This general transfer formula also involves obtaining complex derivatives which may translate into noticeable time lag when the data to be processed increases dramatically over a very short time frame.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

In accordance with a first aspect of the invention there is a method of deriving central aortic systolic pressure comprising the steps of:

a. obtaining a set of predetermined number of blood pressure measurements;
b. reversing the order of the set of predetermined number of blood pressure measurements to obtain a reversed blood pressure set, the reversed blood pressure set representative of a reversed arterial waveform according to the following formula:

$$rbp[1 \ldots n] = bp[n \ldots 1]$$

wherein:
bp represents the set of blood pressure measurements
rbp represents the set of reversed blood pressure measurements
and n represents the predetermined number.
c. determining an integer interval value;
d. averaging a series of consecutive reversed blood pressure measurement readings in the reversed blood pressure set equal to the integer interval value commencing from an $q^{th}$ reversed blood pressure measurement in the reversed blood pressure set;
e. storing the averaged value in an average set;
f. repeat steps d and e with the value of q commencing at 1 and being incremented by 1 each time until the value of q plus the integer interval value equals the predetermined number of blood pressure measurements in the set such that the average set of values represents a moving average waveform;
g. identifying a point of intersection of the reversed arterial waveform and the moving average waveform, and
h. setting the central aortic systolic pressure ($CASP_{final}$) as a reversed blood pressure value $CASP_A$ in the reversed blood pressure set nearest to the point of intersection.

As the intersection point between the reversed arterial waveform and the moving average waveform, is typically at a region on the reversed arterial waveform where the blood pressure measurement density may be higher this may have the advantage of reducing any effects of time lag. Further the central aortic systolic pressure is derived from blood pressure measurements that make no assumptions about the general blood pressure waveform of a cross-representative sample. This may reduce the chances of error.

In accordance with another aspect of the invention there is a method of deriving central aortic systolic pressure comprising the steps of:

a) receiving an arterial waveform dataset
b) dividing the arterial waveform in the arterial waveform dataset into a representative set of blood pressure measurements having a predetermined number;
c) reversing the order of the set of blood pressure measurements having the predetermined number to obtain a reversed blood pressure measurements set, the reversed blood pressure set representative of a reversed arterial waveform according to the following formula:

$$rbp[1 \ldots n] = bp[n \ldots 1]$$

wherein:
bp represents the set of blood pressure measurements
rbp represents the set of reversed blood pressure measurements
and n is the predetermined number.
d) determining an integer interval value for the set being processed;
e) averaging a series of consecutive reversed blood pressure measurement readings in the set equal to the integer interval value commencing from a $q^{th}$ reversed blood pressure measurement in the set;
f) storing the averaged value in an average dataset; the average dataset representative of a moving average waveform;
g) identifying a point of intersection on the reversed arterial waveform and the moving average waveform, and
h) setting the central aortic systolic pressure ($CASP_{final}$) as the reversed blood pressure value $CASP_A$ in the reversed blood pressure set nearest to the point of intersection.

wherein steps b. through h. are repeated for each arterial waveform in the arterial waveform dataset and, for each such repetition, steps e. and f. are further repeated with the value of q commencing at 1 and being incremented by 1 each time until the value of q plus the integer interval value equals the predetermined number of reversed blood pressure measurements in the set being processed.

In accordance with another aspect of the invention there is a method of analysing arterial waveform data to derive a central aortic systolic pressure value comprising the steps of:
a) receiving an arterial waveform dataset, where each arterial waveform in the dataset comprises a representative set of blood pressure measurements having a predetermined number;
b) reversing the order of the representative set of blood pressure measurements to obtain a reversed blood pressure set, the reversed blood pressure set representative of a reversed arterial waveform according to the following formula:

$$rbp[1 \ldots n] = bp[n \ldots 1]$$

wherein:
bp represents the set of blood pressure measurements
rbp represents the set of reversed blood pressure measurements
and n is the predetermined number.
c) determining an integer interval value for the set being processed;
d) averaging a series of consecutive reversed blood pressure measurement readings in the reversed blood pressure set equal to the integer interval value commencing from a $q^{th}$ reversed blood pressure measurement in the set;
e) storing the averaged value in an average dataset, the average dataset representative of a moving average waveform;
f) identifying a point of intersection on the reversed blood pressure set and the moving average waveform, and
g) setting the central aortic systolic pressure ($CASP_{final}$) as the reversed blood pressure value $CASP_A$ in the reversed blood pressure set nearest to the point of intersection, wherein steps b. through g. are repeated for each arterial waveform in the arterial waveform dataset and, for each such repetition, steps d. and e. are further repeated with the value of q commencing at 1 and being incremented by 1 each time until the value of q plus the integer interval value equals the predetermined number of blood pressure measurements in the set being processed.

Preferably setting the central aortic systolic pressure ($CASP_{final}$) further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final} = (CASP_{A1} + CASP_{A2} + CASP_A)/3$$

Preferably the set of blood pressure measurements substantially equates to a uniform distribution of values from the arterial waveform.

Preferably the step of determining the duration of the arterial waveform and where the predetermined number of blood pressure measurements, is determined according to the following formula:

$$\text{Predetermined number} = sr \times t$$

wherein
sr = the sample rate, in Hz, of a measuring device used to record the blood pressure measurements in the set; and
t = the duration of the arterial waveform in seconds Preferably the integer interval value is a division of the sample rate.

In a preferred embodiment the integer interval value is the sample rate divided by 5.

In a preferred embodiment the integer interval value is a division of the predetermined number.

In a preferred embodiment the integer interval value is within a range the boundaries of which are determined as follows:

$$i_{image} = n/(t \times v) \pm (n/(t \times 30))$$

wherein
n is the predetermined number of blood pressure measurements in the set;
t is the duration of the waveform (in seconds); and
v is a predetermined division value.
Preferably the predetermined division value is 5.

In a preferred embodiment the integer interval value is equal to 60 divided by a predetermined division value.

In a preferred embodiment the integer interval value (i) is 12.

In a preferred embodiment the predetermined number of blood pressure measurements in the set is equal to or greater than 12.

In a preferred embodiment the predetermined number of blood pressure measurements in the set is at least 15.

In accordance with another aspect of the invention there is a system for deriving a central aortic systolic pressure comprising:
an arterial waveform measuring device; and
a processing unit,
wherein, the arterial waveform measuring device takes a blood pressure measurement at predetermined intervals until at least one arterial waveform is represented by the set of blood pressure measurements taken, the set of blood pressure measurements representative of one arterial waveform then being communicated to the processing unit which:
a) reverses the order of the blood pressure set to obtain a reversed blood pressure set, the reversed blood pressure set representative of a reversed arterial waveform determined according to the following formula:

$$rbp[1 \ldots n] = bp[n \ldots 1]$$

wherein:
bp represents the set of blood pressure measurements
rbp represents the set of reversed blood pressure measurements
and n is the predetermined number.
b) determines an integer interval value;
c) averages a series of consecutive reversed blood pressure measurement readings in a reversed blood pressure set equal to the integer interval value commencing from a $q^{th}$ reversed blood pressure measurement in the reversed blood pressure set;
d) stores the averaged value in an average set; and
e) identifies a point of intersection on the reversed blood pressure set and the average set, and
f) sets the central aortic systolic pressure ($CASP_{final}$) as the reversed blood pressure value $CASP_A$ in the reversed blood pressure set nearest to the point of intersection.

wherein steps c. and d. are repeated with the value of q commencing at 1 and being incremented by 1 each time until the value of q plus the integer interval value equals the number of blood pressure measurements in the set.

Preferably setting the central aortic systolic pressure ($CASP_{final}$) further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final}=(CASP_{A1}+CASP_{A2}+CASP_A)/3$$

In accordance with another aspect of the invention there is a computer readable medium having software recorded thereon to derive a central aortic systolic pressure, the software comprising:

a means for reversing the order of a set having a predetermined number of blood pressure measurements to obtain a set of reversed blood pressure measurements, the reversed blood pressure measurements representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is the predetermined number;
a first storing means for storing the predetermined number of reversed blood pressure measurements in a reversed blood pressure set;
means for determining an integer interval value;
averaging means to average a series of consecutive reversed blood pressure measurement readings in the reversed blood pressure set equal to the integer interval value commencing from a $q^{th}$ blood pressure measurement in the set;
a second storing means for storing the averaged value in an average set; the average set representative of an average waveform;
an identification means for identifying a point of intersection on the reversed arterial waveform and the average waveform, and
a result means for setting the central aortic systolic pressure ($CASP_{final}$) as the reversed blood pressure value $CASP_A$ in the reversed blood pressure set nearest to the point of intersection.
wherein the functions of the averaging means and the second storing means are repeated with the value of q commencing at 1 and being incremented by 1 each time until the value of q plus the integer interval value equals the predetermined number of blood pressure measurements in the set.

In accordance with another aspect of the invention there is a computer readable medium having software recorded thereon to analyse arterial waveform data to derive a central aortic systolic pressure value comprising, the software comprising:

communication means for receiving an arterial waveform dataset
set means for dividing the arterial waveform in the arterial waveform dataset into a representative set of blood pressure measurements having a predetermined number;
means for reversing the order of the predetermined number of blood pressure measurements to obtain a set of reversed blood pressure measurements, the reversed blood pressure measurements representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is the predetermined number.
interval means for determining an integer interval value for the reversed blood pressure set being processed;
averaging means for averaging a series of consecutive reversed blood pressure measurement readings in the reversed blood pressure set equal to the integer interval value commencing from the $f^{th}$ reversed blood pressure measurement in the set;
first storing means for storing the averaged value in an average set;
an identification means for identifying a point of intersection on the reversed arterial waveform and the average waveform,
a result means for setting the central aortic systolic pressure ($CASP_{final}$) as the reversed blood pressure value $CASP_A$ in the reversed blood pressure set nearest to the reversed blood pressure value at the point of intersection; and
a second storing means for storing the $CASP_{final}$ values at a position corresponding to the position the arterial waveform being processed occupies in the arterial waveform dataset,
wherein the functions of the set means, interval means, averaging means, first storing means and second storing means. are repeated for each arterial waveform in the arterial waveform dataset and, for each such repetition, the functions of the averaging means and first storing means are further repeated with the value of f commencing at 1 and being incremented by 1 each time until the value of f plus the integer interval value equals the predetermined number of blood pressure measurements in the set being processed.

In accordance with another aspect of the invention there is a computer readable medium having software recorded thereon to analyse arterial waveform data to derive a central aortic systolic pressure value, the software comprising:

communication means for receiving an arterial waveform dataset, where each arterial waveform in the dataset comprises a representative set of blood pressure measurements having a predetermined number;
means for reversing the order of the predetermined number of blood pressure measurements to obtain a set of reversed blood pressure measurements, the reversed blood pressure measurements representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is the predetermined number.
interval means for determining an integer interval value for the reversed blood pressure set being processed;
averaging means for averaging a series of consecutive reversed blood pressure measurement readings in the set equal to the integer interval value commencing from a $q^{th}$ reversed blood pressure measurement in the set;
first storing means for storing the averaged value in an average set;
an identification means for identifying a point of intersection on the reversed arterial waveform and the average waveform;
a result means for setting the central aortic systolic pressure ($CASP_{final}$) as the reversed blood pressure value $CASP_A$ in the reversed blood pressure set nearest to the point of intersection; and a second storing means for storing the $CASP_{final}$ value wherein the functions of the interval means, averaging means, first storing means and second storing means. are repeated for each arterial waveform in the arterial waveform dataset and, for each such repetition, the functions of the averaging means and first storing means are further repeated with the value of q commencing at 1 and being incremented by 1 each time until the value of q plus the integer interval value equals the predetermined number of blood pressure measurements in the set being processed.

Preferably setting the central aortic systolic pressure ($CASP_{final}$) further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final}=(CASP_{A1}+CASP_{A2}+CASP_A)/3$$

BRIEF DESCRIPTION OF THE DRAWINGS

The invention will now be described, by way of example only, with reference to the accompanying drawings, in which:

FIG. 3a is a table comprising of test values to produce a corresponding central aortic systolic pressure dataset in accordance with a third embodiment of the present invention.

DESCRIPTION OF EMBODIMENTS OF THE INVENTION

Particular embodiments of the present invention will now be described with reference to the accompanying drawings. The terminology used herein is for the purpose of describing particular embodiments only and is not intended to limit the scope of the present invention. Additionally, unless defined otherwise, all technical and scientific terms used herein have the same meanings as commonly understood by one of ordinary skill in the art to which this invention belongs.

In accordance with a first embodiment of the invention there is provided a method 10 of determining central aortic systolic pressure values. The method 10 is illustrated in flow chart form in FIG. 1.

Figure 1:
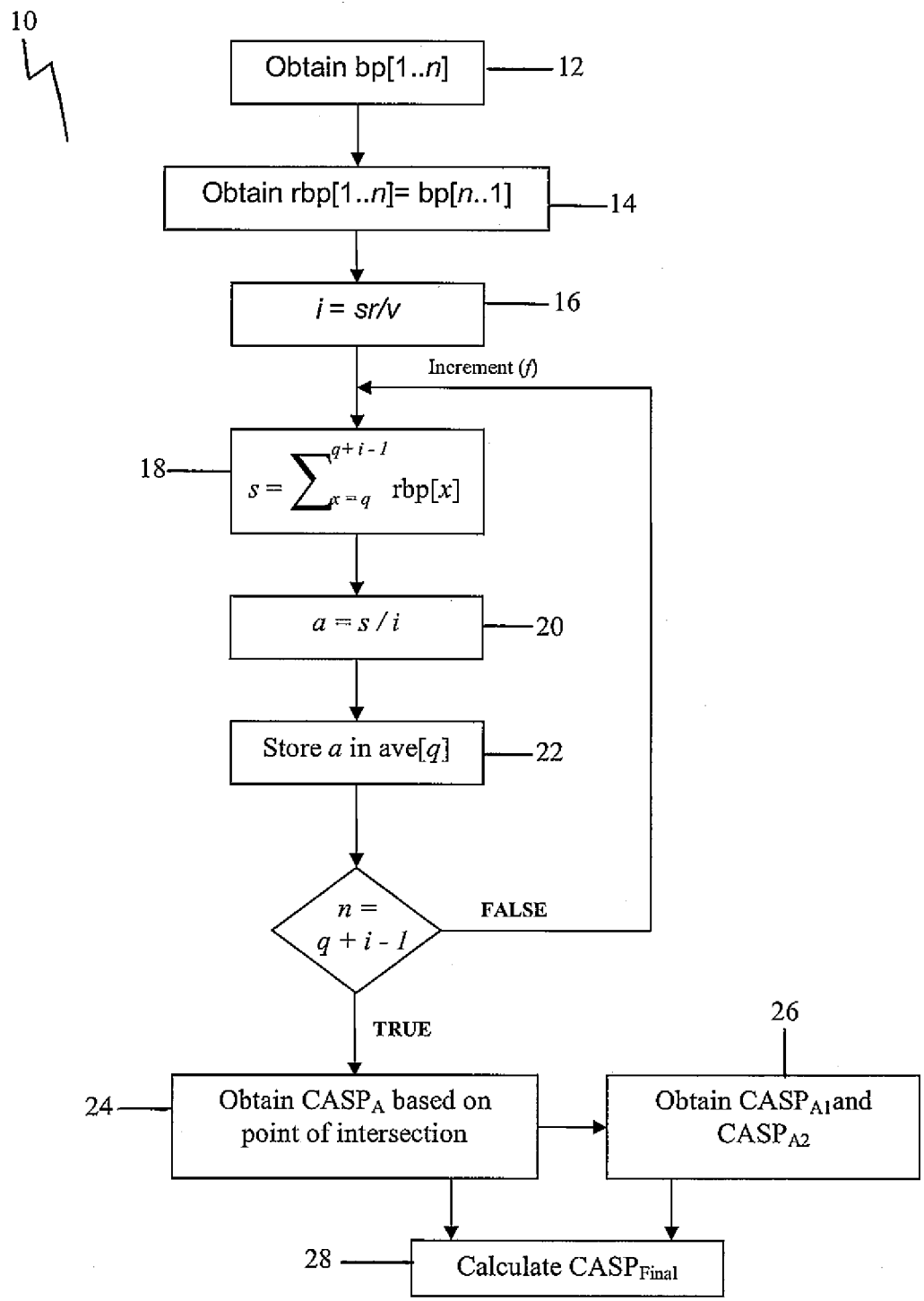
FIG. 1 is a flow chart of a method of determining the central aortic pressure value of an artery in accordance with a first embodiment of the present invention.
Figure 2:
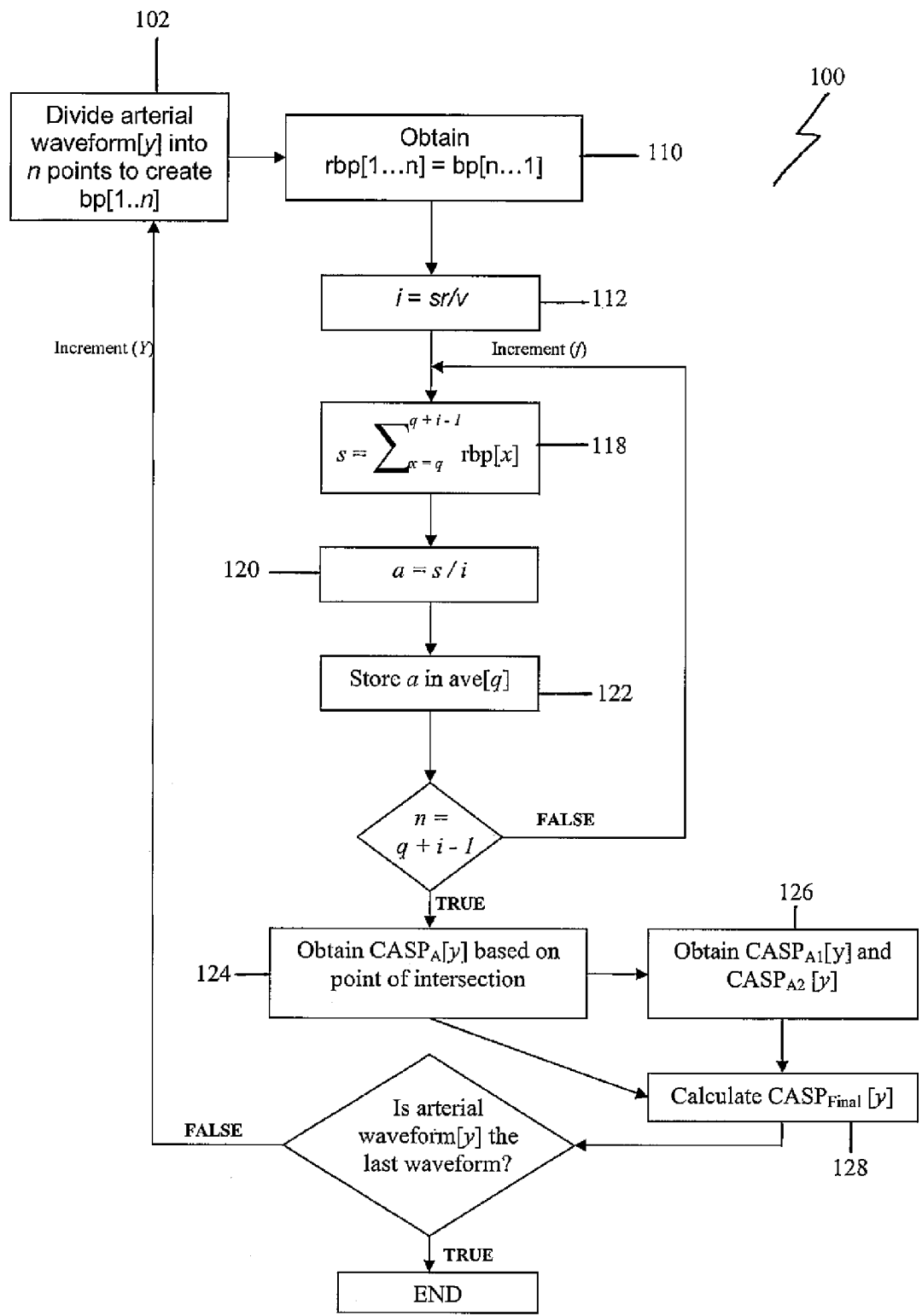
FIG. 2 is a flow chart of a method of analysing an arterial waveform dataset to produce a corresponding central aortic pressure dataset in accordance with a second embodiment of the present invention.

As shown in FIG. 1, the method 10 commences by obtaining a set of blood pressure (bp) measurements representative of an arterial waveform (step 12).

The arterial waveform can be measured at an artery as known in the art and used directly or it may be stored in a database.

The set of blood pressure measurements is reversed in order to obtain a set of reversed blood pressure (rbp) measurement set (step 14) representative of a reversed arterial waveform which is a mirror image of the arterial waveform referenced about a blood pressure axis.

The set of blood pressure/reversed blood pressure measurements has a predetermined number of measurements (n).

The blood pressure and reversed blood pressure measurements relate to each other based on the following formula:

$rbp[1 \ldots n]=bp[n \ldots 1]$ The predetermined number (n) is subsequently divided by the time taken (in seconds) to complete the arterial waveform in order to obtain the sampling rate (sr).

At step 16, the sampling rate (sr) is divided by a predetermined division value (v) to determine an integer interval value (i). In this manner, the integer interval value (i) may be subjected to an absolute or rounding mathematical function.

The following steps are then repeated, commencing with a first reversed blood pressure measurement rbp[(q)]:

At step 18, the reversed blood pressure measurements {rbp[q], rbp[q+1], rbp[q+2], rbp[q+3], ..., rbp[q+i−1]} are summed to form a summed value (s);

At step 20, the summed value (s) is divided by the integer interval value (i) to form an average reversed blood pressure value (a).

At step 22, the average reversed blood pressure value (a) is stored in a moving average set of values.

Steps 18, 20, and 22 are repeated in sequence until the condition [q+i−1] equals predetermined number (n) is met.

The obtained moving average set of values represents a moving average waveform.

Step 24 identifies the reversed blood pressure value ($CASP_A$) on the reversed arterial waveform with a blood pressure value which is nearest to the blood pressure value at the point of intersection between the reversed arterial waveform and the moving average waveform.

In step 26, the central aortic systolic pressure value is determined by locating two points ($CASP_{A1}$ and $CASP_{A2}$) on the reversed arterial waveform adjacent to the reversed blood pressure value ($CASP_A$). At step 28, the central aortic systolic pressure value ($CASP_{final}$) is calculated according to the following formula:

$$CASP_{final}=(CASP_{A1}+CASP_{A2}+CASP_A)/3$$

In accordance with a second embodiment of the present invention there is provided a method 100 of analysing an arterial waveform dataset to produce a corresponding central aortic systolic pressure dataset. A common precursor to this embodiment is that a medical personnel obtains an arterial waveform representation of the blood pressure (bp) of an artery according to any technique as would be known to the person skilled in the art. This arterial waveform representation is then provided to a central processing station for determination of the corresponding central aortic systolic pressure value. Following receipt of the arterial waveform representation, the central processing station operates as follows:

For each arterial waveform in the waveform dataset, a reversed arterial waveform is obtained such that the reversed arterial waveform is a minor image of the arterial waveform referenced about the blood pressure axis.

At step 110, the reversed arterial waveform being processed is divided into a set of representative reversed blood pressure (rbp) measurements. The set of blood pressure measurements and reversed blood pressure measurements has a predetermined number of measurements (n). The blood pressure and reversed blood pressure measurements relate to each other based on the following formula:

$$rbp[1 \ldots n]=bp[n \ldots 1].$$

Each predetermined number (n) is subsequently divided by the time taken (in seconds) to complete the relevant arterial waveform in order to obtain the sampling rate (sr).

At step 112, the sampling rate (sr) is divided by a predetermined division value (v) to determine an integer interval value (i).

The following steps are then repeated, commencing with a first reversed blood pressure measurement rbp[(q)]:

At step 118, the reversed blood pressure measurements {rbp[q], rbp[q+1], rbp[q+2], rbp[q+3], . . . , rbp[q+i−1]} are summed to form a summed value (s);

At step 120, the summed value (s) is divided by the integer interval value (i) to form an average reversed blood pressure value (a).

At step 122, the average reversed blood pressure value (a) is stored in a moving average set.

Steps 118, 120, and 122 are repeated in sequence until the condition [q+i−1] equals predetermined number (n) is met.

The obtained moving average set of values represents a moving average waveform.

Step 124 identifies the reversed blood pressure value ($CASP_A$) on the reversed arterial waveform which is nearest in blood pressure value to the point of intersection between the reversed arterial waveform and the moving average waveform.

In step 126, the central aortic systolic pressure value is obtained by locating two points ($CASP_{A1}$ and $CASP_{A2}$) on the reversed arterial waveform adjacent to the reversed blood pressure value ($CASP_A$). At step 128, the central aortic systolic pressure value ($CASP_{final}$) is then calculated according to the following formula:

$$CASP_{final} = (CASP_{A1} + CASP_{A2} + CASP_A)/3.$$

Steps 110, 112, 118, 120, 122, 124, 126, 128 are then repeated in sequence until such time as a corresponding central aortic systolic pressure value has been calculated for each arterial waveform in the waveform dataset.

In accordance with a third embodiment of the invention, where like numerals reference like steps of the first embodiment, there is provided a method of analysing an arterial waveform dataset to produce a corresponding central aortic systolic pressure value (not shown). This embodiment is based on experiments conducted by the Applicant where it has been found that the predetermined number (n) can be any value in excess of 15.

In this embodiment, while it is preferred that the predetermined division value (v) be 5 to determine an appropriate interval, a substantially accurate aortic systolic pressure value has been able to be obtained where the integer interval value (i) is in a range, the limits of which are determined as follows:

$$i_{range} = n/(t \times v) \pm (n/(t \times 30))$$

where in this embodiment, the variable t is representative of the duration of a single waveform (in seconds).

This embodiment will now be described in more detail in the context of the following example:

In accordance with step 12, a set of blood pressure (bp) measurements from an artery representative of an arterial waveform are obtained. The measurements are depicted in FIG. 3a.

A reversed blood pressure (rbp) measurement set is obtained based on reversing the order of the blood pressure measurement set as depicted in step 14.

The time duration taken to complete this waveform is 0.683 seconds.

In the current embodiment, the predetermined number (n) is set at 41. With a predetermined division value (v) being 5, the integer interval value range (i range) range) is determined as follows:

$$i_{range} = n/(t \times v) \pm (n/(t \times 30)), \text{ therefore}$$

$$i_{range} = 41/(0.683 \times 5) \pm (41/(0.683 \times 30)), \text{ therefore}$$

$$i_{range} = 12.01 \pm (2.00)$$

As it is not possible for intervals to be anything other than integer values, the $i_{range}$ value is restricted to the range of 10 to 14. For the purposes of this example, an integer interval value (i) of 12 shall be used.

Following the requirements of steps 18 through 22, a moving average set of values is obtained.

Figure 3B:
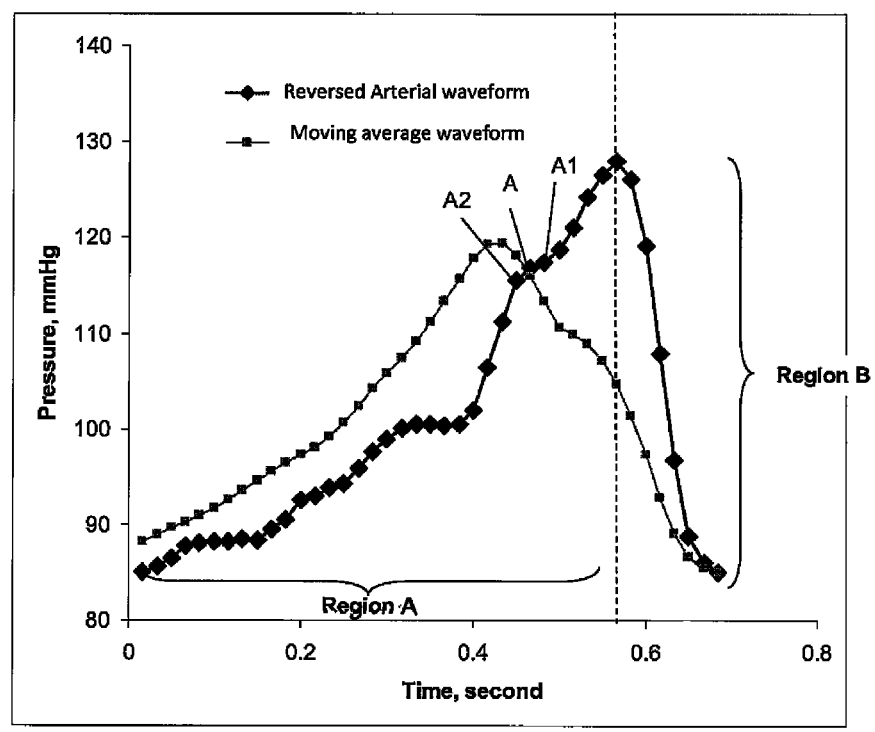
FIG. 3b is a graph depicting the reversed arterial waveform and moving average waveform and their point of intersection that can be processed by any embodiment of the current invention to obtain a central aortic systolic pressure value.

Plotting the moving average set of values and the reversed blood pressure measurements against time, the point of intersection between the average waveform and the reversed arterial waveform is obtained as depicted in FIG. 3b.

$CASP_A$ is the nearest blood pressure value to the point of intersection between the reversed arterial waveform and the moving average waveform. As can be seen from the plot, the $CASP_A$ value is 116.8. $CASP_{A1}$ and $CASP_{A2}$ are the two blood pressure values adjacent to the $CASP_A$ on the reversed arterial waveform. As can be seen from the plot, the $CASP_{A1}$ value is 115.6 and the $CASP_{A2}$ value is 117.5.

The calculated $CASP_{final}$ value is (115.6+117.5+116.8)/3=116.6 mmHg

In a fourth, and most preferred embodiment of the invention, there is provided a method of determining central aortic systolic pressure value as described in the first embodiment of the invention. However, in this embodiment, the predetermined number (n) is determined according to the following formula:

$$n = sr \times t$$

where
sr=the sample rate (in hertz) of a measuring device used to record the blood pressure measurements in the set bp; and
t=the time taken (in seconds) to complete one arterial waveform.

In this embodiment, the blood pressure measurements in the set bp are the measurement values taken by the measuring device at each repetition of the sample rate. Furthermore, in this embodiment of the invention, the interval value is in a range, the limits of which are determined as follows:

$$i_{range} = sr/v \pm (sr/30)$$

In this case, sr again represents the sample rate (in hertz) of a measuring device used to record the blood pressure measurements in the set bp. Additionally, the predetermined division value (v) is preferably 5. This formula is only applicable though when the value (sr) is in excess of 15. The minimum limit should be 15 however for the purposes of illustration, a value of 30 is used in the preferred embodiments.

Using the same set of blood pressure measurements as set out above, but this time in a situation where the set is the culmination of blood pressure values taken by a sampling device having a sample rate (sr) of 60 measurements per second, the $i_{range}$ value is calculated as follows:

$$i_{range} = sr/v \pm (sr/30)$$

$$i_{range} = 60/5 \pm (60/30)$$

$$i_{range} = 12 \pm 2$$

This results in an $i_{range}$ value of between 10 and 14. The remaining steps of the method can then proceed as set out in the first embodiment above.

In all the embodiments described, the intersection point between the reversed arterial waveform and the moving average waveform typically occurs at a region on the reversed arterial waveform where the blood pressure measurements density is higher. This is region A of FIG. 3a. As contrasted to region B, the blood pressure measurements density is higher in region A. Region A and B depicts the relevant portion of the curves and are not measurements based on horizontal or vertical reference.

It should be appreciated by the person skilled in the art that the above invention is not limited to the embodiments described. In particular, the following modifications and improvements may be made without departing from the scope of the present invention:

The set of blood pressure measurements may be obtained from a device that is also adapted to perform the method of the present invention. Alternatively, the set of blood pressure measurements may be obtained from a separate device and communicated to a further apparatus adapted to perform the method of the present invention.

The second embodiment of the invention may be modified such that the waveform dataset data may contain sets of data representative of waveforms.

The waveform dataset may be supplied to the entity performing the method along with the duration of each waveform in the dataset. Alternatively, the entity performing the method may determine the duration of each waveform independently through alternate means (such as by receiving graphs having a fixed time value for predetermined lengths of the x axis and approximating the duration of the waveform based on this time/distance relationship or by deriving the duration from other composite values, such as the sample rate used to generate the set of blood pressure measurements).

To be the most representative of an arterial waveform, the blood pressure values that form the set bp should be of uniform distribution along the arterial waveform.

The central aortic systolic pressure value ($CASP_{final}$) may be identified as the averaged value ($CASP_A$) in the central aortic systolic pressure set nearest to the point of intersection between the reversed arterial waveform and the moving average waveform. i.e. $CASP_{final}=CASP_A$.

Other ways of obtaining intersection point may be used. These include using derivative methods, solving simultaneous equations and other mathematical tools used to identify the intersection points between two waveforms.

The means of obtaining the moving average may be achieved by other methods such as obtaining median or other such methods that will have the effect of smoothening the reverse arterial waveform.

It should be further appreciated by the person skilled in the art that the features described above, where not mutually exclusive, can be combined to form yet further embodiments of the invention.

We claim:

1. A method of deriving a central aortic systolic pressure, the method comprising:
   utilizing a processor configured to:
   a. obtain a set of predetermined number of blood pressure measurements representative of an arterial waveform;
   b. reverse an order of the set of predetermined number of blood pressure measurements to obtain a reversed blood pressure set, the reversed blood pressure set representative of a reversed arterial waveform according to the following formula:

$rbp[1 \ldots n]=bp[n \ldots 1]$ wherein:
   bp represents the set of blood pressure measurements
   rbp represents the set of reversed blood pressure measurements
   and n represents the predetermined number;
   c. determine an integer interval value;
   d. average a series of consecutive reversed blood pressure measurement readings in the reversed blood pressure set equal to the integer interval value commencing from an $q^{th}$ reversed blood pressure measurement in the reversed blood pressure set;
   e. storing the averaged value in an average set;
   f. repeat steps d and e with the value of q commencing at 1 and being incremented by 1 each time until the value of q plus the integer interval value equals the predetermined number of blood pressure measurements in the set such that the average set of values represents a moving average waveform;
   g. identify a point of intersection of the reversed arterial waveform and the moving average waveform, and
   h. set the central aortic systolic pressure ($CASP_{final}$) as a reversed blood pressure value $CASP_A$ in the reversed blood pressure set nearest to the point of intersection.

2. The method according to claim 1, wherein the step h further comprises the steps of locating two points ($CASP_{A1}$ and $CASP_{A2}$) on the reversed arterial waveform adjacent to the point $CASP_A$; the $CASP_{final}$ determined according to the formula:

$CASP_{final}=(CASP_{A1}+CASP_{A2}+CASP_A)/3.$

3. The method according to claim 1, wherein the set of blood pressure measurements substantially equates to a uniform distribution of values from the arterial waveform.

4. The method according to claim 3, wherein the processor is further configured to determine the duration of the arterial waveform and where the predetermined number of blood pressure measurement is determined according to the following formula:

Predetermined number=$sr \times t$ wherein
sr=the sample rate, in Hz, of a measuring device used to record the blood pressure measurements in the set; and
t=the duration of the arterial waveform in seconds.

5. The method according to claim 4, wherein the integer interval value is a division of the sample rate.

6. The method according to claim 5, wherein the integer interval value is the sample rate divided by 5.

7. The method according to claim 1, wherein the integer interval value is a division of the predetermined number.

8. The method according to claim 7, wherein the integer interval value is within a range the boundaries of which are determined as follows:

$i_{range}=n/(t \times v) \pm (n/(t \times 30))$ wherein
n is the predetermined number of blood pressure measurements in the set;
t is the duration of the waveform (in seconds); and
v is a predetermined division value.

9. The method according to claim 8, wherein the predetermined division value is 5.

10. The method according to claim 1, wherein the integer interval value is equal to 60 divided by a predetermined division value.

11. The method according to claim 10, wherein the integer interval value (i) is 12.

12. The method according to claim 1, wherein the predetermined number of blood pressure measurements in the set is equal to or greater than 12.

13. The method according to claim 12, wherein the predetermined number of blood pressure measurements in the set is at least 15.

14. A method of analysing arterial waveform data to derive a central aortic systolic pressure value, the method comprising:
utilizing a processor configured to:
a) receive an arterial waveform dataset;
b) divide the arterial waveform in the arterial waveform dataset into a representative set of blood pressure measurements having a predetermined number of measurements;
c) reverse an order of the set of blood pressure measurements having the predetermined number of measurements to obtain a reversed blood pressure measurements set, the reversed blood pressure set representative of a reversed arterial waveform according to the following formula:

$$rbp[1\ldots n]=bp[n\ldots 1]$$

wherein:
bp represents the set of blood pressure measurements
rbp represents the set of reversed blood pressure measurements
and n is the predetermined number;
d) determine an integer interval value for the set being processed;
e) average a series of consecutive reversed blood pressure measurement readings in the set equal to the integer interval value commencing from a $q^{th}$ reversed blood pressure measurement in the set;
f) store the averaged value in an average dataset; the average dataset representative of a moving average waveform;
g) identify a point of intersection on the reversed arterial waveform and the moving average waveform, and
h) set the central aortic systolic pressure ($CASP_{final}$) as the reversed blood pressure value $CASP_A$ in the reversed blood pressure set nearest to the point of intersection;
wherein steps b. through h. are repeated for each arterial waveform in the arterial waveform dataset and, for each such repetition, steps e. and f. are further repeated with the value of q commencing at 1 and being incremented by 1 each time until the value of q plus the integer interval value equals the predetermined number of reversed blood pressure measurements in the set being processed.

15. The method according to claim 14 wherein the step h further comprises the steps of locating two points ($CASP_{A1}$ and $CASP_{A2}$) on the arterial waveform adjacent to the point $CASP_A$; the $CASP_{final}$ determined according to the formula:

$$CASP_{final}=(CASP_{A1}+CASP_{A2}+CASP_A)/3.$$

16. The method of deriving the central aortic systolic pressure according to claim 14, wherein the integer interval value is equal to 60 divided by a predetermined division value.

17. The method of deriving the central aortic systolic pressure according to claim 16, wherein the integer interval value is 12.

18. The method of analysing arterial waveform data to derive the central aortic systolic pressure value according to claim 14, wherein the predetermined number of blood pressure measurements in the set is equal to or greater than 12.

19. The method of analysing arterial waveform data to derive the central aortic systolic pressure value according to claim 18, wherein the predetermined number of blood pressure measurements in the set is at least 15.

20. A method of analysing arterial waveform data to derive a central aortic systolic pressure value, the method comprising:
utilizing a processor configured to:
a) receive an arterial waveform dataset, where each arterial waveform in the arterial waveform dataset comprises a representative set of blood pressure measurements having a predetermined number of measurements;
b) reverse an order of the representative set of blood pressure measurements to obtain a reversed blood pressure set, the reversed blood pressure set representative of a reversed arterial waveform according to the following formula:

$$rbp[1\ldots n]=bp[n\ldots 1]$$

wherein:
bp represents the set of blood pressure measurements
rbp represents the set of reversed blood pressure measurements
and n is the predetermined number;
c) determine an integer interval value for the set being processed;
d) average a series of consecutive reversed blood pressure measurement readings in the reversed blood pressure set equal to the integer interval value commencing from a $q^{th}$ reversed blood pressure measurement in the set;
e) store the averaged value in an average dataset, the average dataset representative of a moving average waveform;
f) identify a point of intersection on the reversed blood pressure set and the moving average waveform, and
g) set the central aortic systolic pressure ($CASP_{final}$) as the reversed blood pressure value $CASP_A$ in the reversed blood pressure set nearest to the point of intersection,
wherein steps b. through g. are repeated for each arterial waveform in the arterial waveform dataset and, for each such repetition, steps d. and e. are further repeated with the value of q commencing at 1 and being incremented by 1 each time until the value of q plus the integer interval value equals the predetermined number of blood pressure measurements in the set being processed.

21. The method according to claim 20, where the step g further comprises the steps of locating two points ($CASP_{A1}$ and $CASP_{A2}$) on the reversed blood pressure set adjacent to the point $CASP_A$; the $CASP_{final}$ determined according to the formula:

$$CASP_{final}=(CASP_{A1}+CASP_{A2}+CASP_A)/3.$$

22. The method according to claim 20, wherein the predetermined number of blood pressure measurements for at least one arterial waveform in the dataset differs from the predetermined number of blood pressure measurements for the other arterial waveforms in the dataset.

23. The method according to claim 20, where the set of blood pressure measurements substantially equates to a uniform distribution of values from the arterial waveform.

24. The method according to claim 23, wherein the processor is further configured to determine the duration of the arterial waveform and where the predetermined number of blood pressure measurement is determined according to the following formula:

$$\text{Predetermined number}=sr\times t$$

wherein
sr=the sample rate, in Hz, f a measuring device used to record the blood pressure measurements in the set; and
t=the duration of the arterial waveform.

25. The method according to claim 20, wherein the integer interval value is a division of the sample rate.

26. The method according to claim 25, wherein the integer interval value is the sample rate divided by 5.

27. The method according to claim 20, wherein the integer interval value is a division of the predetermined number.

28. The method according to claim 27, wherein the integer interval value is within a range the boundaries of which are determined as follows:

$$i_{range}=n/(t\times v)\pm(n/(t\times 30))$$

wherein
n is the predetermined number of blood pressure measurements in the set;
t is the duration of the waveform (in seconds); and
v is a predetermined division value.

29. The method according to claim 28, wherein the predetermined division value is 5.

30. A system for deriving a central aortic systolic pressure comprising:
an arterial waveform measuring device; and
a processing unit,
wherein, the arterial waveform measuring device takes a blood pressure measurement at predetermined intervals until at least one arterial waveform is represented by the set of blood pressure measurements taken, the set of blood pressure measurements representative of one arterial waveform then being communicated to the processing unit which:
a) reverses the order of the blood pressure set to obtain a reversed blood pressure set, the reversed blood pressure set representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is a predetermined number;
b) determines an integer interval value;
c) averages a series of consecutive reversed blood pressure measurement readings in a reversed blood pressure set equal to the integer interval value commencing from a $q^{th}$ reversed blood pressure measurement in the reversed blood pressure set;
d) stores the averaged value in an average set; and
e) identifies a point of intersection on the reversed blood pressure set and the average set, and
f) sets the central aortic systolic pressure ($CASP_{final}$) as the reversed blood pressure value $CASP_A$ in the reversed blood pressure set nearest to the point of intersection;
wherein steps c. and d. are repeated with the value of q commencing at 1 and being incremented by 1 each time until the value of q plus the integer interval value equals the number of blood pressure measurements in the set.

31. The system according to claim 30 wherein the step f further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final}=(CASP_{A1}+CASP_{A2}+CASP_A)/3.$$

32. A non-transitory computer readable medium having software recorded thereon to derive a central aortic systolic pressure, the software comprising:

a means for reversing the order of a set having a predetermined number of blood pressure measurements to obtain a set of reversed blood pressure measurements, the reversed blood pressure measurements representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is the predetermined number;
a first storing means for storing the predetermined number of reversed blood pressure measurements in a reversed blood pressure set;
means for determining an integer interval value;
averaging means to average a series of consecutive reversed blood pressure measurement readings in the reversed blood pressure set equal to the integer interval value commencing from a $q^{th}$ blood pressure measurement in the set;
a second storing means for storing the averaged value in an average set; the average set representative of an average waveform;
an identification means for identifying a point of intersection on the reversed arterial waveform and the average waveform, and
a result means for setting the central aortic systolic pressure ($CASP_{final}$) as the reversed blood pressure value $CASP_A$ in the reversed blood pressure set nearest to the point of intersection;
wherein the functions of the averaging means and the second storing means are repeated with the value of q commencing at 1 and being incremented by 1 each time until the value of q plus the integer interval value equals the predetermined number of blood pressure measurements in the set.

33. The computer readable medium according to claim 32, wherein the results means further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final}=(CASP_{A1}+CASP_{A2}+CASP_A)/3.$$

34. A non-transitory computer readable medium having software recorded thereon to analyse arterial waveform data to derive a central aortic systolic pressure value comprising, the software comprising:
communication means for receiving an arterial waveform dataset set means for dividing the arterial waveform in the arterial waveform dataset into a representative set of blood pressure measurements having a predetermined number;
means for reversing the order of the predetermined number of blood pressure measurements to obtain a set of reversed blood pressure measurements, the reversed blood pressure measurements representative of a reversed arterial waveform determined according to the following formula:

$$rbp[1\ldots n]=bp[n\ldots 1]$$

wherein:
bp represents the set of blood pressure measurements
rbp represents the set of reversed blood pressure measurements
and n is the predetermined number;

interval means for determining an integer interval value for the reversed blood pressure set being processed;

averaging means for averaging a series of consecutive reversed blood pressure measurement readings in the reversed blood pressure set equal to the integer interval value commencing from the $f^{th}$ reversed blood pressure measurement in the set;

first storing means for storing the averaged value in an average set;

an identification means for identifying a point of intersection on the reversed arterial waveform and the average waveform, a result means for setting the central aortic systolic pressure ($CASP_{final}$) as the reversed blood pressure value $CASP_A$ in the reversed blood pressure set nearest to the reversed blood pressure value at the point of intersection; and a second storing means for storing the $CASP_{final}$ values at a position corresponding to the position the arterial waveform being processed occupies in the arterial waveform dataset, wherein the functions of the set means, interval means, averaging means, first storing means and second storing means are repeated for each arterial waveform in the arterial waveform dataset and, for each such repetition, the functions of the averaging means and first storing means are further repeated with the value of f commencing at 1 and being incremented by 1 each time until the value of f plus the integer interval value equals the predetermined number of blood pressure measurements in the set being processed.

35. The computer readable medium according to claim 34, wherein the results means further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final} = (CASP_{A1} + CASP_{A2} + CASP_A)/3.$$

36. A non-transitory computer readable medium having software recorded thereon to analyse arterial waveform data to derive a central aortic systolic pressure value, the software comprising:

communication means for receiving an arterial waveform dataset, where each arterial waveform in the dataset comprises a representative set of blood pressure measurements having a predetermined number;

means for reversing the order of the predetermined number of blood pressure measurements to obtain a set of reversed blood pressure measurements, the reversed blood pressure measurements representative of a reversed arterial waveform determined according to the following formula:

$$rbp[1 \ldots n] = bp[n \ldots 1]$$

wherein:

bp represents the set of blood pressure measurements rbp represents the set of reversed blood pressure measurements and n is the predetermined number;

interval means for determining an integer interval value for the reversed blood pressure set being processed;

averaging means for averaging a series of consecutive reversed blood pressure measurement readings in the set equal to the integer interval value commencing from a $q^{th}$ reversed blood pressure measurement in the set;

first storing means for storing the averaged value in an average set;

an identification means for identifying a point of intersection on the reversed arterial waveform and the average waveform;

a result means for setting the central aortic systolic pressure ($CASP_{final}$) as the reversed blood pressure value $CASP_A$ in the reversed blood pressure set nearest to the point of intersection; and a second storing means for storing the $CASP_{final}$ value wherein the functions of the interval means, averaging means, first storing means and second storing means are repeated for each arterial waveform in the arterial waveform dataset and, for each such repetition, the functions of the averaging means and first storing means are further repeated with the value of q commencing at 1 and being incremented by 1 each time until the value of q plus the integer interval value equals the predetermined number of blood pressure measurements in the set being processed.

37. The computer readable medium according to claim 36, wherein the results means further comprises the steps of locating two points ($CASP_{A1}$ and $CASP_{A2}$) on the reversed arterial waveform adjacent to the point $CASP_A$; the $CASP_{final}$ determined according to the formula:

$$CASP_{final} = (CASP_{A1} + CASP_{A2} + CASP_A)/3.$$

* * * * *